US011883502B2

(12) United States Patent
Winters et al.

(10) Patent No.: US 11,883,502 B2
(45) Date of Patent: Jan. 30, 2024

(54) METHODS FOR PRODUCTION OF CAPSULAR POLYSACCHARIDE PROTEIN CONJUGATES FROM *STREPTOCOCCUS PNEUMONIAE* SEROTYPE 19F (71) Applicant: Merck Sharp & Dohme LLC, Rahway, NJ (US)

(72) Inventors: Michael Albert Winters, Doylestown, PA (US); John E. MacNair, Lansdale, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/544,239

(22) Filed: Dec. 7, 2021

(65) Prior Publication Data

US 2022/0088210 A1    Mar. 24, 2022

Related U.S. Application Data (63) Continuation of application No. 16/482,337, filed as application No. PCT/US2018/015905 on Jan. 30, 2018, now abandoned.

(60) Provisional application No. 62/452,521, filed on Jan. 31, 2017.

(51) Int. Cl.
A61K 47/64    (2017.01)
A61K 39/09    (2006.01)
A61K 47/36    (2006.01)
G01N 33/569    (2006.01)
A61K 39/00    (2006.01)

(52) U.S. Cl.
CPC .......... *A61K 47/646* (2017.08); *A61K 39/092* (2013.01); *A61K 47/36* (2013.01); *G01N 33/56944* (2013.01); *A61K 2039/6037* (2013.01); *G01N 2333/315* (2013.01)

(58) Field of Classification Search
None
See application file for complete search history.

(56) References Cited

U.S. PATENT DOCUMENTS

| | | | |
|---|---|---|---|
| 4,365,170 A | 12/1982 | Okuhara | |
| 4,673,574 A | 6/1987 | Anderson | |
| 4,902,506 A | 2/1990 | Anderson et al. | |
| 5,623,057 A | 4/1997 | Marburg et al. | |
| 6,146,902 A | 11/2000 | McMaster | |
| 2007/0184071 A1 | 8/2007 | Hausdorff et al. | |
| 2007/0253984 A1 | 11/2007 | Khandke et al. | |
| 2011/0195086 A1 | 8/2011 | Caulfield et al. | |
| 2013/0072881 A1* | 3/2013 | Khandke | A61P 31/04 424/197.11 |
| 2013/0273098 A1 | 10/2013 | Blue et al. | |
| 2015/0231270 A1 | 8/2015 | Prasad | |
| 2015/0265702 A1 | 9/2015 | Biemans et al. | |
| 2015/0328328 A1 | 11/2015 | Han et al. | |
| 2020/0222550 A1 | 7/2020 | Winters et al. | |
| 2022/0088210 A1 | 3/2022 | Winters et al. | |

FOREIGN PATENT DOCUMENTS

| | | |
|---|---|---|
| CA | 2358022 A1 | 7/2000 |
| CN | 103391714 A | 11/2013 |
| CN | 103893751 A | 7/2014 |
| CN | 104870463 A | 8/2015 |
| CN | 106102770 A | 11/2016 |
| CN | 109804075 A | 5/2019 |
| CN | 110337307 A | 10/2019 |
| CN | 111050794 A | 4/2020 |
| CN | 111065388 A | 4/2020 |
| CN | 112074293 A | 12/2020 |
| CN | 112533940 A | 3/2021 |
| CN | 114728050 A | 7/2022 |
| EP | 471177 B1 | 10/1995 |
| WO | 9315760 A1 | 8/1993 |
| WO | 9508348 A1 | 3/1995 |
| WO | 1996029094 A1 | 9/1996 |
| WO | 9842721 A1 | 3/1998 |
| WO | 2000038711 A2 | 7/2000 |
| WO | 2006110381 A1 | 10/2006 |
| WO | 2007068907 A2 | 6/2007 |
| WO | 2007071707 A2 | 6/2007 |
| WO | 2007071710 A2 | 6/2007 |
| WO | 2007071711 A2 | 6/2007 |
| WO | 2007071786 A2 | 6/2007 |
| WO | 2007116028 A2 | 10/2007 |
| WO | 2008043774 A1 | 4/2008 |
| WO | 2008128939 A1 | 10/2008 |
| WO | 2011100151 A1 | 8/2011 |
| WO | 2011110531 A2 | 9/2011 |
| WO | 2012078482 A1 | 6/2012 |

(Continued)

OTHER PUBLICATIONS

"Room temperature," Merriam-Webster.com Dictionary, https://www.merriam-webster.com/dictionary/room%20temperature. Accessed Jan. 28, 2021 (2 pages).

Bahy, Rehab H. et al., Development and evaluation of a novel vaccine against prevalent invasive multi-drug resistant strains of *treptococcus pneumoniae*, PeerJ, 2016, 1-15, 4:(e2737).

Chiayung Chu et al., Further Studies on the Immunogenicity of Haemophilus influenzae Type b and Pneumococcal Type 6A Polysaccharide-Protein Conjugates, Infection and Immunity, Apr. 1983, 245-256.

(Continued)

*Primary Examiner* — Oluwatosin A Ogunbiyi (74) *Attorney, Agent, or Firm* — Matthew A. Leff; Alysia A. Finnegan (57) ABSTRACT The present invention provides a method of producing a polysaccharide-protein conjugate with capsular polysaccharide from *Streptococcus pneumoniae* serotype 19F conjugated to a carrier protein. The method includes a prolonged incubation step prior to filtration to remove free polysaccharide.

8 Claims, 3 Drawing Sheets

(56) References Cited

FOREIGN PATENT DOCUMENTS

| WO | 2012119972 | A1 | 9/2012 |
|---|---|---|---|
| WO | 2012173876 | A1 | 12/2012 |
| WO | 2014097099 | A2 | 6/2014 |
| WO | 2015110941 | A2 | 7/2015 |
| WO | 2017220753 | A1 | 12/2017 |
| WO | 2018026547 | A1 | 2/2018 |
| WO | 2018144438 | A1 | 8/2018 |
| WO | 2018144439 | A1 | 8/2018 |
| WO | 2018156465 | A1 | 8/2018 |
| WO | 2018156467 | A1 | 8/2018 |
| WO | 2018156468 | A1 | 8/2018 |
| WO | 2018156491 | A1 | 8/2018 |
| WO | 2019036313 | A1 | 2/2019 |
| WO | 2019050814 | A1 | 3/2019 |
| WO | 2019183290 | A1 | 9/2019 |
| WO | 2019212846 | A1 | 11/2019 |
| WO | 2021021729 | A1 | 2/2021 |
| WO | 2022101745 | A2 | 5/2022 |

OTHER PUBLICATIONS

Geoffry S. Bethell et al., A Novel Method of Activation of Cross-linked Agaroses with 1,1'-Carbonyldiimidazole Which Gives a Matrix for Affinity Chromatography Devoid of Additional Charged Groups, The Journal of Biological Chemistry, 1979, 2572-2574, 254-8.

Lei, Q.P. et al., Quantification of Free Polysaccharide in Meningococcal Polysaccharide-Diphtheria Toxoid Conjugate Vaccines, Dev. Biol., 2000, 259-264, 103.

Michael J. Gidley et al., Reductive methylation of proteins with sodium cyanoborohydride, Biochem, 1982, 331-334, 203.

Milton T. W. Hearn et al., Application of 1,1'-Carbonyldiimidazole-activated Matrices for the purification of proteins, Journal of Chromatography, 1981, 509-518, 218.

Neil Jentoft et al., Protein Labeling by Reductive Methylation with Sodium Cyanoborohydride: Effect of Cyanide and Metal Ions on the Reaction, Analytical Biochemistry, 1980, 186-190, 106.

Smith, William J. et al., Analytical technology development to monitor the stability of Polysaccharide-Protein conjugate vaccines, Vaccine, 2022, 4182-4189, 40.

U.S. Appl. No. 16/482,337, filed Jul. 31, 2019.

\* cited by examiner

METHODS FOR PRODUCTION OF CAPSULAR POLYSACCHARIDE PROTEIN CONJUGATES FROM *STREPTOCOCCUS PNEUMONIAE* SEROTYPE 19F

FIELD OF INVENTION

The present invention relates to a method of producing a pneumococcal serotype 19F capsular polysaccharide protein conjugate. In particular, the method provides for greater stability of polysaccharide protein conjugates having pneumococcal serotype 19F by providing a prolonged incubation time after conjugation and prior to filtration. The invention also relates to the preparation of a multivalent pneumococcal conjugate vaccine comprising stable serotype 19F polysaccharide protein conjugate.

BACKGROUND OF THE INVENTION

Polysaccharide-protein conjugate vaccines, comprising bacterial capsular polysaccharides conjugated to carrier proteins have been developed and additional ones are in development. Examples of developed conjugate vaccines include the *Haemophilus influenzae* type b (Hib) conjugate vaccine (e.g., HIBTITER®) as well as conjugate vaccines against *Streptococcus pneumoniae* (e.g., PREVNAR® and PREVNAR 13®) and *Neisseria meningitidis* (e.g., MENJUGATE®).

Upon the conjugation of a polysaccharide antigen to a carrier protein, the reaction mixture can be purified to remove free polysaccharide that has no protein conjugated thereto, free carrier protein that has no polysaccharide antigen conjugated thereto, and low molecular weight polysaccharide protein conjugates. Various methods for the purification of free polysaccharide, free protein, and low molecular weight conjugates are known in the art, including hydrophobic chromatography, tangential ultrafiltration, diafiltration etc. See, e.g., International Patent Application Publication No. WO00/38711, U.S. Pat. No. 6,146,902, and Lei et al., 2000, Dev. Biol. 103:259-264.

There is a continuing need for improved methods of producing stable polysaccharide protein conjugates and purifying polysaccharide protein conjugates from impurities such as free polysaccharide and low molecular weight conjugates.

SUMMARY OF THE INVENTION

The present invention provides methods for the production and purification of a polysaccharide-protein conjugate comprising *Streptococcus pneumoniae* serotype 19F capsular polysaccharide covalently linked to a carrier protein from a mixture comprising polysaccharide-protein conjugate and free polysaccharide, the method comprising the steps of:
  a) incubating said mixture for a minimum of 6 hours, at a temperature ranging from 2-30° C., in a buffer having a pH in the range of 5.0 to 9.0; and
  b) performing size separation under conditions that allow removal of free polysaccharide.

In certain embodiments, the size separation uses a nominal molecular weight cut off (NMWCO) membrane of from 100 to 500 kDa whereby the polysaccharide-protein conjugate is retained in the retentate.

In certain embodiments, the methods further comprise c) collecting the polysaccharide-protein conjugate.

The methods described herein are applicable to carrier proteins including but not limited to tetanus toxoid, diphtheria toxoid, and $CRM_{197}$. In certain embodiments of the invention, the carrier protein is $CRM_{197}$.

In certain embodiments, the retained polysaccharide-protein conjugate has an average molecular weight of 600 kDa or more, or 1000 kDa or more.

In certain embodiments, the pH of the incubation is in the range from 5.8 to 7.0. The buffer employed in the methods of the invention can be selected from a phosphate buffer, histidine, or TRIS and have a pH in the range of pH 5.8 to 7.0. In one embodiment, the buffer has a pH of 7.0.

In certain embodiments, the temperature of incubation is controlled in the range of 4-25° C.

In certain embodiments, the size separation is by size-exclusion chromatography, bind/elute chromatography, or wide-pore ultrafiltration. In one aspect, the size separation is by wide-pore ultrafiltration with a membrane having a NMWCO of 100 kDa to 300 kDa.

In certain embodiments, the incubation proceeds for at least 12 hours or at least 20 hours, for example, between 108 to 132 hours.

The present invention also provides methods for formulating the polysaccharide-protein conjugate with one or more additional polysaccharide-protein conjugates from a different serotype. In one embodiment, the methods further comprise formulating with an adjuvant.

DETAILED DESCRIPTION OF THE INVENTION

The present invention is based in part on the discovery that traditional methods, including ultrafiltration, were insufficient to provide a stable polysaccharide-protein conjugate for *S. pneumoniae* serotype 19F. Specifically, the 19F conjugate was found to be unstable and had reduced potency. As shown in the Examples, Applicants' work demonstrated that after conjugation of serotype 19F polysaccharide to $CRM_{197}$, the conjugated 19F polysaccharide is prone to degradation, resulting in product that has elevated free polysaccharide levels and reduced conjugate size. A plateau of between 25-30% free polysaccharide was obtained whether at 4° C. (after approximately 3 months) or 22° C.-25° C. (after approximately 5-7 days).

Without being bound by any theory, this degradation event is believed to be due to the presence of labile sites on the 19F polysaccharide. By allowing degradation of the labile sites to occur, through a prolonged incubation time after conjugation and prior to purification, the resulting conjugate can be stabilized so that the free polysaccharide content, conjugate size, and conjugate potency do not change over time.

Accordingly, the present invention describes a method for the production of a polysaccharide-protein conjugate comprising Streptococcus pneumoniae serotype 19F covalently linked to a carrier protein from a mixture comprising polysaccharide-protein conjugate and free polysaccharide by incubating said mixture for 6 hours or longer, 12 hours or longer, 20 hours or longer or 24 hours or longer in an appropriate buffer (such as phosphate, histidine, or any buffer with a pKa in the range of 6-9); and performing a purification step, such as wide-pore ultrafiltration, under conditions that allow removal of free polysaccharide, and optionally collecting the polysaccharide-protein antigen from the retentate. The free polysaccharide may optionally be collected from the ultrafiltration permeate and re-used in a conjugation reaction, if desired.

The conjugation reaction mixture may comprise polysaccharide antigen-carrier protein conjugates and free polysaccharide. The mixture may also contain free carrier protein, low molecular weight conjugates and other proteins. The method of the invention provides polysaccharide-protein conjugates of higher stability.

The invention further provides a method of preparing an immunogenic composition by mixing the purified polysaccharide-protein conjugate from serotype 19F with additional polysaccharide-protein conjugates from additional S. pneumoniae serotypes.

As used herein, the term "comprises" when used with the immunogenic composition of the invention refers to the inclusion of any other components (subject to limitations of "consisting of" language for the antigen mixture), such as adjuvants and excipients. The term "consisting of" when used with the multivalent polysaccharide-protein conjugate mixture refers to a mixture having those particular S. pneumoniae polysaccharide protein conjugates and no other S. pneumoniae polysaccharide protein conjugates from a different serotype.

As used herein, the phrase "drug product" refers to the formulated blend of polysaccharide-carrier protein conjugates from two or more serotypes.

As used herein, the phrase "drug substance" refers to the individual polysaccharide-carrier protein conjugate from a given serotype.

As used herein, the phrase "polysaccharide-protein conjugate from serotype" refers to a conjugate having a S. pneumoniae capsular polysaccharide obtained from the specified serotype, e.g., 19F, and a carrier protein, e.g., $CRM_{197}$.

As used herein, ranges used for, for example, pH and temperature, are meant to be inclusive. For example, a pH range from 5.0 to 9.0 is meant to include a pH of 5.0 and a pH of 9.0. Similarly, a temperature range from 4 to 25° C. is meant to include the outer limits of the range, i.e., 4° C. and 25° C.

Streptococcus pneumoniae Capsular Polysaccharides

Capsular polysaccharides from Streptococcus pneumoniae, including serotype 19F, can be prepared by standard techniques known to those skilled in the art. For example, polysaccharides can be isolated from bacteria and may be sized to some degree by known methods (see, e.g., European Patent Nos. EP497524 and EP497525); and preferably by microfluidisation accomplished using a homogenizer or by chemical hydrolysis. In certain techniques, S. pneumoniae strains corresponding to each polysaccharide serotype are grown in a soy-based medium. The individual polysaccharides are then purified through standard steps including centrifugation, precipitation, and ultrafiltration. See, e.g., U.S. Patent Application Publication No. 2008/0286838 and U.S. Pat. No. 5,847,112. Polysaccharides can be sized in order to reduce viscosity and/or to improve filterability and the lot-to-lot consistency of subsequent conjugated products. Capsular polysaccharides can also be prepared from one or more of serotypes 1, 2, 3, 4, 5, 6A, 6B, 6C, 7C, 7F, 8, 9N, 9V, 10A, 11A, 12F, 14, 15A, 15B, 15C, 16F, 17F, 18C, 19A, 20, 22F, 23A, 23B, 23F, 24F, 33F, 35B, 35F, or 38 for inclusion in multivalent pneumococcal polysaccharide protein conjugate vaccines.

Carrier Protein

In a particular embodiment of the present invention, $CRM_{197}$ is used as the carrier protein. $CRM_{197}$ is a non-toxic variant (i.e., toxoid) of diphtheria toxin. In one embodiment, it is isolated from cultures of Corynebacterium diphtheria strain C7 (β197) grown in casamino acids and yeast extract-based medium. In another embodiment, $CRM_{197}$ is prepared recombinantly in accordance with the methods described in U.S. Pat. No. 5,614,382. Typically, $CRM_{197}$ is purified through a combination of ultra-filtration, ammonium sulfate precipitation, and ion-exchange chromatography. In some embodiments, $CRM_{197}$ is prepared in Pseudomonas fluorescens using Pfenex Expression Technology™ (Pfenex Inc., San Diego, CA).

Other suitable carrier proteins include additional inactivated bacterial toxins such as DT (Diphtheria toxoid), TT (tetanus toxoid) or fragment C of TT, pertussis toxoid, cholera toxoid (e.g., as described in International Patent Application Publication No. WO 2004/083251), E. coli LT, E. coli ST, and exotoxin A from Pseudomonas aeruginosa. Bacterial outer membrane proteins such as outer membrane complex c (OMPC), porins, transferrin binding proteins, pneumococcal surface protein A (PspA; See International Application Patent Publication No. WO 02/091998), pneumococcal surface adhesin protein (PsaA), C5a peptidase from Group A or Group B streptococcus, or Haemophilus influenzae protein D, pneumococcal pneumolysin (Kuo et al., 1995, Infect Immun 63; 2706-13) including ply detoxified in some fashion for example dPLY-GMBS (See International Patent Application Publication No. WO 04/081515) or dPLY-formol, PhtX, including PhtA, PhtB, PhtD, PhtE and fusions of Pht proteins for example PhtDE fusions, PhtBE fusions (See International Patent Application Publication Nos. WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from N. meningitidis), PD (Haemophilus influenzae protein D; see, e.g., European Patent No. EP 0 594 610 B), or immunologically functional equivalents thereof, synthetic peptides (See European Patent Nos. EP0378881 and EP0427347), heat shock proteins (See International Patent Application Publication Nos. WO 93/17712 and WO 94/03208), pertussis proteins (See International Patent Application Publication No. WO 98/58668 and European Patent No. EP0471177), cytokines, lymphokines, growth factors or hormones (See International Patent Application Publication No. WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, Infect Immun 72:4884-7), iron uptake proteins (See International Patent Application Publication No. WO 01/72337), toxin A or B of *C. difficile* (See International Patent Publication No. WO 00/61761), and flagellin (See Ben-Yedidia et al., 1998, Immunol Lett 64:9) can also be used as carrier proteins.

Other DT mutants can be used, such as $CRM_{176}$, $CRM_{228}$, $CRM_{45}$ (Uchida et al., 1973, J Biol Chem 218:3838-3844); $CRM_9$, $CRM_{45}$, $CRM_{102}$, $CRM_{103}$ and $CRM_{107}$ and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. Nos. 4,709,017 or 4,950,740; mutation of at least one or more residues Lys 516, Lys 526, Phe 530 and/or Lys 534 and other mutations disclosed in U.S. Pat. Nos. 5,917,017 or 6,455,673; or fragments disclosed in U.S. Pat. No. 5,843,711.

Polysaccharide-Protein Conjugation

The purified polysaccharides are typically chemically activated to introduce functionalities capable of reacting with the carrier protein. Once activated, each capsular polysaccharide is separately conjugated to a carrier protein to form a glycoconjugate. The polysaccharide conjugates may be prepared by known coupling techniques.

In one embodiment, the chemical activation of the polysaccharides and subsequent conjugation to the carrier protein are achieved by means described in U.S. Pat. Nos. 4,365,170, 4,673,574 and 4,902,506. Briefly, the pneumococcal polysaccharide is reacted with a periodate-based oxidizing agent such as sodium periodate, potassium periodate, or periodic acid resulting in random oxidative cleavage of vicinal hydroxyl groups to generate reactive aldehyde groups.

Direct aminative coupling of the oxidized polysaccharide to primary amine groups on the protein carrier (mainly lysine residues) can be accomplished by reductive amination. For example, conjugation is carried out by reacting a mixture of the activated polysaccharide and carrier protein with a reducing agent such as sodium cyanoborohydride in the presence of nickel. The conjugation reaction may be carried out in aqueous solution or in an organic solvent such as dimethylsulfoxide (DMSO). See, e.g., US2015/0231270 A1, EP 0471 177 B1, US2011/0195086 A1. At the conclusion of the conjugation reaction, unreacted aldehydes are optionally reduced by addition of a strong reducing agent, such as sodium borohydride.

In one embodiment, prior to formulation, each pneumococcal capsular polysaccharide antigen is individually purified from *S. pneumoniae*, activated to form reactive aldehydes, and then covalently conjugated to a carrier protein using reductive amination with sodium cyanoboroydride in the presence of nickel. Nickel forms complexes with residual, interfering cyanide from the sodium cyanoborohydride reducing agent used for reductive amination. Thus, nickel is used in the methods of the invention for greater conjugation reaction efficiency and to aid in free cyanide removal.

Transition metals are known to form stable complexes with cyanide and are known to improve reductive methylation of protein amino groups and formaldehyde with sodium cyanoborohydride. See Gidley et al., *Biochem J*. 1982, 203: 331-334; Jentoft et al. *Anal Biochem*. 1980, 106: 186-190. However, Applicants surprisingly found that by complexing residual, interfering cyanide, the addition of nickel increases the consumption of protein during the conjugation of and leads to formation of larger, potentially more immunogenic conjugates.

Variability in free cyanide levels in commercial sodium cyanoborohydride reagent lots may lead to inconsistent conjugation performance, resulting in variable conjugate attributes, including molecular mass and polysaccharide-to-protein ratio. The addition of nickel to the conjugation reaction reduces the level of free cyanide and thus improves the degree of lot-to-lot conjugate consistency.

In another embodiment, the conjugation method may employ activation of polysaccharide with 1-cyano-4-dimethylamino pyridinium tetrafluoroborate (CDAP) to form a cyanate ester. The activated saccharide may be coupled directly to an amino group on the carrier protein.

In an alternative embodiment, a reactive homobifunctional or heterobifunctional group may be introduced on the activated polysaccharide by reacting the cyanate ester with any of several available modalities. For example, cystamine or cysteamine may be used to prepare a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Such conjugates are described in International Patent Application Publication Nos. WO 93/15760, WO 95/08348 and WO 96/29094; and Chu et al., 1983, Infect. Immunity 40:245-256.

Other suitable conjugation methods use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by reaction with carrier protein to form a carbamate linkage. This chemistry consists of reduction of the anomeric terminus of a carbohydrate to form a primary hydroxyl group followed by reaction of the primary hydroxyl with CDI to form a carbamate intermediate and subsequent coupling to protein carrier amino groups. The reaction may require optional protection/deprotection of other primary hydroxyl groups on the saccharide.

Following conjugation, the polysaccharide-protein conjugates are purified to remove excess conjugation reagents as well as residual free protein and free polysaccharide by one or more of any techniques well known to the skilled artisan, including concentration/diafiltration operations, ultrafiltration, precipitation/elution, column chromatography, and depth filtration. See, e.g., U.S. Pat. No. 6,146,902.

For serotype 19F, it was discovered that there was a rapid decline in potency over time indicating relative instability of the conjugated material. This was found to be associated with an increase in free polysaccharide and a decrease in conjugate size. In order to overcome these issues, it was discovered that an incubation period after the conjugation prior to purification using, for example, a wide-pore ultrafiltration step to remove free polysaccharide improved the stability of the polysaccharide protein conjugate. This increase in free polysaccharide is believed to be due to the presence of labile sites on the 19F polysaccharide. By incubating 19F polysaccharide after conjugation (and prior to purification), the portion of 19F polysaccharide prone to degradation (~25-30%) can be allowed to degrade and be removed by a filtration step.

The incubation conditions should be chosen to allow the 19F polysaccharide to degrade through its labile sites, but not include conditions which would degrade the polysaccharide through other mechanisms, such as excessively high or low pH. As shown in the Examples, degradation of non-incubated 19F conjugate to free polysaccharide reached the plateau of about 30% at about 3 months at 4° C. and at about 7 days at 25° C. It is readily apparent that time and temperature (and pH) can be varied under a number of different conditions to obtain the maximum degradation of that portion of the conjugate containing labile sites.

The incubation can take for as long as five days or longer, for example, 5 to 7 days, to achieve optimal removal of free Ps. However, significant reduction for free Ps can be achieved in as little as one day. Accordingly, the present invention provides methods where the incubation occurs for a minimum of 1, 3, 6, 12, 18, 24, 36, 48, 60 or 72 hours. The incubation can occur for up to 60, 72, 84, 96, 108, 120, or 132 hours. The present invention encompasses all combination of these incubation times including for example, 6 to 96 hours, 24 to 84 hours, 48 to 60 hours, as well as 72 hours to 132 hours, 96 hours to 132 hours and 108 hours to 132 hours. It would be expected that times greater than 132 hours, e.g., 150 hours, 180 hours, 200 hours, 240 hours and greater, could be used with minimal effect on the degradation. Generally, a higher degradation rate will be seen at higher temperatures so when higher temperatures are used, the incubation time can be shorter.

The incubation preferably takes place in the buffer used for conjugation or following conjugation. The buffer can be selected from histidine, phosphate, TRIS or any buffer with a pH in the range of 6.0-9.0, 6.0 to 8.5, or 6.5 to 7.5. In certain embodiments, the buffer has a pH of 6.0, 6.5, 7.0, 7.5, 8.0, 8.5 or 9.0.

The buffer optionally further contains a salt selected from sodium and potassium chloride. Ranges of salt concentrations are from 0-500 mM. In one embodiment, the buffer is 10 mM histidine or 25 mM potassium phosphate and further includes 150 mM sodium chloride.

The pH of the incubation can occur between a pH from 5.0 to 9.0, 5.8 to 7.0, or 7.0±0.2.

The temperature of the incubation can occur between 2-30° C., 4-25° C., 15-25° C., or 20-25° C. As discussed above, at higher temperatures, the kinetics of degradation occurs more quickly. With higher temperatures, the incubation times can be shorter. Conversely, at lower temperatures, the kinetics of degradation occurs more slowly. With lower temperatures, the incubation times are generally longer.

After conjugation of the capsular polysaccharide to the carrier protein, the polysaccharide-protein conjugates are purified (enriched with respect to the amount of polysaccharide-protein conjugate of the desired size range, e.g., by removing free polysaccharide) by size separation using one or more of a variety of techniques. Examples of these techniques are well known to the skilled artisan and include concentration/diafiltration operations, ultrafiltration including wide-pore ultrafiltration, precipitation/elution, column chromatography including size-exclusion and bind/elute chromatography, and depth filtration. See, e.g., U.S. Pat. No. 6,146,902. The appropriate molecular weight cut off can be selected from 100 kDa to 500 kDa, e.g., 100 kDa, 200 kDa, 250 kDa, 300 kDa, 400 kDa or 500 kDa. In particular embodiments, the size separation is accomplished by wide-pore ultrafiltration with a membrane having a MWCO of 100 kDa to 300 kDa.

Purification not only removes free polysaccharide but can also remove low molecular weight conjugates thereby increasing the overall average molecular weight of the polysaccharide-protein conjugates. In some embodiments, the average molecular weight of the retained conjugates is 600 kDa, 700 kDa, 800 kDa, 900 kDa, or 1000 kDa or more.

The polysaccharide protein conjugate can then be collected from the retentate on the filter or column using standard techniques.

Following the purification step, the product is typically 0.2-micron filtered in preparation for formulation.

Pharmaceutical/Vaccine Compositions

The serotype 19F conjugate prepared using the methods of the invention can be used in compositions, including pharmaceutical, immunogenic and vaccine compositions, comprising, consisting essentially of, or alternatively, consisting of any polysaccharide serotype combinations together with a pharmaceutically acceptable carrier and an adjuvant. For example, the compositions can comprise, consist essentially of, or consist of 2 to 35, e.g., 13, 14, 15, 16, 17, 18, 19, 20, 21, 22, 23, 24, 25, 26, 27, 28, 29, 30, 31, 32, 33, 34 or 35 distinct polysaccharide-protein conjugates, wherein each of the conjugates contains a different capsular polysaccharide conjugated individually to one or more carrier proteins, and wherein the capsular polysaccharides (in addition to 19F) further comprise at least one of serotypes 1, 2, 3, 4, 5, 6A, 6B, 6C, 7C, 7F, 8, 9N, 9V, 10A, 11A, 12F, 14, 15A, 15B, 15C, 16F, 17F, 18C, 19A, 20, 22F, 23A, 23B, 23F, 24F, 33F, 35B, 35F, or 38 of *Streptococcus pneumonia*, together with a pharmaceutically acceptable carrier and an adjuvant. In certain embodiments, the carrier protein is $CRM_{197}$.

After the individual glycoconjugates are prepared, purified and filtered, as described above, they are compounded using standard techniques to formulate the immunogenic composition of the present invention. These pneumococcal conjugates are prepared by separate processes and bulk formulated into a single dosage formulation.

Formulation of the polysaccharide-protein conjugates of the present invention can be accomplished using art-recognized methods. For instance, 9, 11, 13, 15 or more individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In a preferred embodiment, the vaccine composition is formulated in L-histidine buffer with sodium chloride.

As defined herein, an "adjuvant" is a substance that serves to enhance the immunogenicity of an immunogenic composition of the invention. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (International Patent Application Publication No. WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, MA), (b) SAF, containing 10% Squalene, 0.4% Tween 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, MT) containing 2% Squalene, 0.2% Tween 80, and one or more bacterial cell wall components from the group consisting of 3-O-deaylated monophosphorylipid A (MPL™) described in U.S. Pat. No. 4,912,094, trehalose dimycolate (TDM), and cell wall skeleton (CWS), preferably MPL+CWS (Detox™); and (d) a Montanide ISA;

(3) saponin adjuvants, such as Quil A or STIMULON™ QS-21 (Antigenics, Framingham, MA) (see, e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O-[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion (5) synthetic polynucleotides such as oligonucleotides containing CpG motif(s) (U.S. Pat. No. 6,207,646); and (6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc; and (7) complement, such as a trimer of complement component C3d.

In another embodiment, the adjuvant is a mixture of 2, 3, or more of the above adjuvants, e.g.,. SBAS2 (an oil-in-water emulsion also containing 3-deacylated monophosphoryl lipid A and QS21).

Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). The aluminum salt includes, but is not limited to, hydrated alumina, alumina hydrate, alumina trihydrate (ATH), aluminum hydrate, aluminum trihydrate, alhydrogel, Superfos, Amphogel, aluminum (III) hydroxide, aluminum hydroxyphosphate sulfate (Aluminum Phosphate Adjuvant (APA)), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a monodisperse particle size distribution. The product is then diafiltered against physiological saline and steam sterilized.

In certain embodiments, a commercially available $Al(OH)_3$ (e.g. Alhydrogel or Superfos of Denmark/Accurate Chemical and Scientific Co., Westbury, NY) is used to adsorb proteins. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of antigen that is released slowly over a period of 2-3 weeks, be involved in nonspecific activation of macrophages and complement activation, and/or stimulate innate immune mechanism (possibly through stimulation of uric acid). See, e.g., Lambrecht et al., 2009, Curr Opin Immunol 21:23.

In certain embodiments, monovalent bulk aqueous conjugates are typically blended together and diluted to target 8 μg/mL for all serotypes except 6B, if used, which will be diluted to target 16 μg/mL. Once diluted, the batch will be filter sterilized, and an equal volume of aluminum phosphate adjuvant added aseptically to target a final aluminum concentration of 250 μg/mL. The adjuvanted, formulated batch will typically be filled into single-use, 0.5 mL/dose vials.

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

"CpG-containing nucleotide," "CpG-containing oligonucleotide," "CpG oligonucleotide," and similar terms refer to a nucleotide molecule of 6-50 nucleotides in length that contains an unmethylated CpG moiety. See, e.g., Wang et al., 2003, Vaccine 21:4297. In another embodiment, any other art-accepted definition of the terms is intended. CpG-containing oligonucleotides include modified oligonucleotides using any synthetic internucleoside linkages, modified base and/or modified sugar.

Methods for use of CpG oligonucleotides are well known in the art and are described, for example, in Sur et al., 1999, J Immunol. 162:6284-93; Verthelyi, 2006, Methods Mol Med. 127:139-58; and Yasuda et al., 2006, Crit Rev Ther Drug Carrier Syst. 23:89-110.

Administration/Dosage

The compositions and formulations of the present invention can be used to protect or treat a human susceptible to infection, e.g., a pneumococcal infection, by means of administering the vaccine via a systemic or mucosal route. In one embodiment, the present invention provides a method of inducing an immune response to a *S. pneumoniae* capsular polysaccharide conjugate, comprising administering to a human an immunologically effective amount of an immunogenic composition of the present invention. In another embodiment, the present invention provides a method of vaccinating a human against a pneumococcal infection, comprising the step of administering to the human an immunologically effective amount of an immunogenic composition of the present invention.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

"Effective amount" of a composition of the invention refers to a dose required to elicit antibodies that significantly reduce the likelihood or severity of infectivity of a microbe, e.g., S. pneumonia, during a subsequent challenge.

The composition of the invention can be used for the prevention and/or reduction of primary clinical syndromes caused by microbes, e.g., S. pneumonia, including both invasive infections (meningitis, pneumonia, and bacteremia), and noninvasive infections (acute otitis media, and sinusitis).

Administration of the compositions of the invention can include one or more of: injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage).

The amount of conjugate in each vaccine dose is selected as an amount that induces an immunoprotective response without significant, adverse effects. Such amount can vary depending upon the pneumococcal serotype. Generally, for polysaccharide-based conjugates, each dose will comprise 0.1 to 100 μg of each polysaccharide, particularly 0.1 to 10 μg, and more particularly 1 to 5 μg. For example, each dose can comprise 100, 150, 200, 250, 300, 400, 500, or 750 ng or 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 μg.

In one embodiment, the dose of the aluminum salt is 10, 15, 20, 25, 30, 50, 70, 100, 125, 150, 200, 300, 500, or 700 μg, or 1, 1.2, 1.5, 2, 3, 5 mg or more. In yet another embodiment, the dose of alum salt described above is per μg of recombinant protein.

The compositions described herein are preferably administered to a human subject. In certain embodiments, the human patient is an infant (less than 1 year of age), toddler (approximately 12 to 24 months), or young child (approximately 2 to 5 years). In other embodiments, the human patient is an elderly patient (>65 years). The compositions of this invention are also suitable for use with older children, adolescents and adults (e.g., aged 18 to 45 years or 18 to 65 years).

A composition described herein can be administered as a single inoculation. The vaccine can be administered twice, three times or four times or more, adequately spaced apart. For example, the composition may be administered at 1, 2, 3, 4, 5, or 6 month intervals or any combination thereof. The immunization schedule can follow that designated for pneumococcal vaccines. For example, the routine schedule for infants and toddlers against invasive disease caused by S. pneumoniae is 2, 4, 6 and 12-15 months of age. Thus, in a preferred embodiment, the composition is administered as a 4-dose series at 2, 4, 6, and 12-15 months of age.

The compositions may also include one or more proteins from S. pneumoniae. Examples of S. pneumoniae proteins suitable for inclusion include those identified in International Patent Application Publication Nos. WO 02/083855 and WO 02/053761.

Formulations

The compositions described herein can be administered to a subject by one or more method known to a person skilled in the art, such as parenterally, transmucosally, transdermally, intramuscularly, intravenously, intra-dermally, intra-nasally, subcutaneously, intra-peritonealy, and formulated accordingly.

In one embodiment, compositions can be administered via epidermal injection, intramuscular injection, intravenous, intra-arterial, subcutaneous injection, or intra-respiratory mucosal injection of a liquid preparation. Liquid formulations for injection include solutions and the like.

The composition can be formulated as single dose vials, multi-dose vials or as pre-filled syringes.

Compositions described herein can be administered orally, and would thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or non-aqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The pharmaceutical composition may be isotonic, hypotonic or hypertonic. However it is often preferred that a pharmaceutical composition for infusion or injection is essentially isotonic, when it is administrated. Hence, for storage the pharmaceutical composition may preferably be isotonic or hypertonic. If the pharmaceutical composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to sodium chloride (NaCl), calcium chloride ($CaCl_2$), potassium chloride (KCl) and magnesium chloride ($MgCl_2$). Examples of non-ionic isotonic agents include but are not limited to mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

The buffer may for example be selected from the group consisting of TRIS, acetate, glutamate, lactate, maleate, tartrate, phosphate, citrate, carbonate, glycinate, histidine, glycine, succinate and triethanolamine buffer.

The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and TRIS.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The DP formulations described herein may also contain a surfactant. Preferred surfactants include, but are not limited to: the polyoxyethylene sorbitan esters surfactants (commonly referred to as the Tweens); copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy) polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate.

Mixtures of surfactants can be used, e.g. PS80/Span 85 mixtures. A combination of a polyoxyethylene sorbitan ester such as polyoxyethylene sorbitan monooleate (PS80) and an octoxynol such as t-octylphenoxypolyethoxyethanol (Triton X-100) is also suitable. Another useful combination comprises laureth 9 plus a polyoxyethylene sorbitan ester and/or an octoxynol.

Analytical

For pneumococcal conjugate vaccines, release and stability testing is important for quality control. Each polysaccharide-protein conjugate in a commercial lot is tested against a reference standard to ensure the appropriate dose and/or potency. Stable reference standards ensure consistent and robust testing results for both release and stability testing. If a reference standard degrades over time, the test results generated in a relative assay, such as those often used to measure potency, will drift over time.

Applicants' work with 19F showed that additional incubation prior to purification improved its stability. Thus, the use of 19F conjugate made by the process described herein as a reference standard would better ensure consistent test results over time and enable better method precision and accuracy. If 19F conjugate not subject to this additional incubation step were used as a reference standard, the degradation seen with 19F could introduce systematic bias into the test results.

Thus, in certain embodiments, the present invention is also directed to polysaccharide protein conjugate immunoassays for measuring dose and/or potency in a pneumococcal conjugate vaccine manufacturing lot using 19F conjugate as a reference standard. Such immunoassays include the sandwich ELISA described in the Analytical section of the Examples.

Having described various embodiments of the invention with reference to the accompanying description and drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLES

Analytical Methods

Molecular Weight and Concentration Analysis of Conjugates Using HPSEC/UV/MALS/RI Assay Conjugate samples were injected and separated by high performance size-exclusion chromatography (HPSEC). Detection was accomplished with ultraviolet (UV), multi-angle light scattering (MALS) and refractive index (RI) detectors in series. Protein concentration was calculated from $A_{280}$ (absorbance at 280 nm) using an extinction coefficient. Polysaccharide concentration was deconvoluted from the RI signal (contributed by both protein and polysaccharide) using the dn/dc factors which are the change in a solution's refractive index with a change in the solute concentration reported in mL/g. Average molecular weight of the samples were calculated by Astra software (Wyatt Technology Corporation, Santa Barbara, CA) using the measured concentration and light scattering information across the entire sample peak. There are multiple forms of average values of molecular weight for polydispersed molecules. For example, number-average molecular weight Mn, weight-average molecular weight Mw, and z-average molecular weight Mz (Molecules, 2015, 20, 10313-10341). Unless specified, the molecular weights are weight-average molecular weight.

Free Polysaccharide Testing

Free polysaccharide (polysaccharide that is not conjugated with $CRM_{197}$) in conjugate sample was measured by first precipitating free protein and conjugates with deoxycholate (DOC) and hydrochloric acid. Precipitates were then filtered out and the filtrates were analyzed for free polysaccharide concentration by HPSEC/UV/MALS/RI. Free polysaccharide is calculated as a percentage of total polysaccharide measured by HPSEC/UV/MALS/RI.

Total Polysaccharide ELISA

The Total Polysaccharide (Ps) Sandwich ELISA is a multi-valent immunoassay intended to measure the total amount of polysaccharide in drug product samples. Ps is captured and detected by serotype-specific antibodies, and the polysaccharide content is compared relative to a standard by parallel line analysis of dilution curves. Serotype-specific antibodies are first coated directly on the microtiter plate. After a blocking step, dilution curves of standards and samples are applied to the coated microtiter plates. Immobilized polysaccharides are detected with a mix of serotype-specific antibodies and a secondary antibody conjugated to alkaline phosphatase (AP Conjugate). A fluorescent signal is developed with 4-Methylumbelliferyl phosphate (4-MuP).

Example 1: Preparation of S. Pneumoniae Capsular Polysaccharides

Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EP0497524. Isolates of pneumococcal subtypes are available from the American Type Culture Collection (Manassas, VA). The bacteria are identified as encapsulated, non-motile, Gram-positive, lancet-shaped diplococci that are alpha-hemolytic on blood-agar. Subtypes can be differentiated on the basis of Quelling reaction using specific antisera. See, e.g., U.S. Pat. No. 5,847,112.

Cell banks representing each of the S. pneumococcus serotypes present were obtained from the Merck Culture Collection (Rahway, NJ) in a frozen vial. A thawed seed culture was transferred to the seed fermentor containing a pre-sterilized growth media appropriate for S. pneumoniae. The culture was grown in the seed fermentor with temperature and pH control. The entire volume of the seed fermentor was transferred to a production fermentor containing pre-sterilized growth media. The production fermentation was the final cell growth stage of the process. Temperature, pH, and the agitation rate were controlled.

The fermentation process was terminated via the addition of an inactivating agent. After inactivation, the batch was transferred to the inactivation tank where it was held at controlled temperature and agitation. Cell debris was removed using a combination of centrifugation and filtration. The batch was ultrafiltered and diafiltered. The batch was then subjected to solvent-based fractionations that remove impurities and recover polysaccharide.

Example 2: Conjugation of Serotypes 1, 3, 4, 5, 6A, 6B, 7F, 9V, 14, 18C, 19A, 19F, 22F, 23F, and 33F to $CRM_{197}$ Using Reductive Amination in Aqueous Solution The different serotype polysaccharides were individually conjugated to purified $CRM_{197}$ carrier protein using a common process flow. Polysaccharide was dissolved, size reduced, chemically activated and buffer-exchanged by ultrafiltration. Purified $CRM_{197}$ was then conjugated to the activated polysaccharide utilizing $NiCl_2$ (2 mM) in the reaction mixture, and the resulting conjugate was purified by ultrafiltration prior to a final 0.2-micron filtration. Several process parameters within each step, such as pH, temperature, concentration, and time were controlled to serotype-specific values as described in the sections below.

Polysaccharide Size Reduction and Activation

Purified pneumococcal capsular Ps powder was dissolved in water, and all serotypes, except serotype 19A, were 0.45-micron filtered. All serotypes, except serotype 19A, were homogenized to reduce the molecular mass of the Ps. Serotype 19A was not size reduced due to its relatively low starting size. Homogenization pressure and number of passes through the homogenizer were controlled to serotype-specific targets (150-1000 bar; 4-7 passes) to achieve a serotype-specific molecular mass. Size-reduced polysaccharide was 0.2-micron filtered and then concentrated and diafiltered against water using a 10 kDa NMWCO tangential flow ultrafiltration membrane.

The polysaccharide solution was then adjusted to a serotype-specific temperature (4-22° C.) and pH (4-5) with sodium acetate buffer to minimize Ps size reduction during the activation step. Polysaccharide activation was performed via periodate oxidation. For serotype 4, prior to activation, the batch was incubated at approximately 50° C. and pH 4.0 to partially deketalize the Ps. Ps activation was initiated with the addition of a sodium metaperiodate solution. The amount of sodium metaperiodate added was serotype-specific, ranging from approximately 0.1 to 0.5 moles of sodium metaperiodate per mole of polysaccharide repeating unit. The serotype-specific charge of sodium metaperiodate was selected to achieve a target level of Ps activation (moles aldehyde per mole of Ps repeating unit).

For all serotypes, with the exception of serotypes 5 and 7F, the activated product was diafiltered against 10 mM potassium phosphate, pH 6.4, using a 10 kDa NMWCO tangential flow ultrafiltration membrane. Serotypes 5 and 7F were diafiltered against 10 mM sodium acetate, pH 4-5. Ultrafiltration for all serotypes was conducted at 2-8° C.

Polysaccharide Conjugation to $CRM_{197}$

Oxidized polysaccharide solution was mixed with water and 1.5 M potassium phosphate, buffered at either pH 6.0 or pH 7.0, depending on the serotype. The buffer pH was selected to optimize stability of activated Ps during the conjugation reaction. Purified $CRM_{197}$, obtained through expression in Pseudomonas fluorescens as previously described (WO 2012/173876 A1), was 0.2-micron filtered and combined with the buffered polysaccharide solution at a polysaccharide to $CRM_{197}$ mass ratio ranging from 0.4 to 1.0 w/w depending on the serotype. The mass ratio was selected to control the polysaccharide to $CRM_{197}$ ratio in the resulting conjugate. The polysaccharide and phosphate concentrations were serotype-specific, ranging from 3.6 to 10.0 g/L and 100 to 150 mM, respectively, depending on the serotype. The serotype-specific Ps concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for a serotype-specific duration (72 to 120 hours) in order to maximize consumption of Ps and protein.

Reduction with Sodium Borohydride

Following the conjugation reaction, the batch was diluted to a Ps concentration of approximately 3.5 g/L, cooled to 2-8° C., and 1.2-micron filtered. All serotypes (except serotype 5) were diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g Ps/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was then added. Serotype 5 was diafiltered against 300 mM sodium bicarbonate, pH 9, using a 100 kDa NMWCO tangential flow ultrafiltration membrane and then pH-neutralized.

Sterile Filtration and Product Storage

The batch was then concentrated and diafiltered against 10 mM histidine in 150 mM sodium chloride, pH 7.0 at 4° C. using a 300 kDa NMWCO tangential flow ultrafiltration membrane. The retentate batch was 0.2-micron filtered.

Serotype 19F was incubated for approximately 7 days at 22° C., diafiltered against 10 mM histidine in 150 mM sodium chloride, pH 7.0 at 4° C. using a 100 kDa NMWCO tangential flow ultrafiltration membrane, and 0.2-micron filtered.

The batch was adjusted to a Ps concentration of 1.0 g/L with additional 10 mM histidine in 150 mM sodium chloride, pH 7.0. The batch was dispensed into aliquots and frozen at ≤−60° C.

Example 3: Methods for the Conjugation of Serotypes 6A, 6B, 7F, 9V, 18C, 19A, 19F, 22F, 23F and 33F to $CRM_{197}$ Using Reductive Amination in Dimethylsulfoxide The different serotype polysaccharides were individually conjugated to the purified $CRM_{197}$ carrier protein using a common process flow. Polysaccharide was dissolved, sized to a target molecular mass, chemically activated and buffer-exchanged by ultrafiltration. Activated polysaccharide and purified $CRM_{197}$ were individually lyophilized and redissolved in dimethylsulfoxide (DMSO). Redissolved polysaccharide and $CRM_{197}$ solutions were then combined and conjugated as described below. The resulting conjugate was purified by ultrafiltration prior to a final 0.2-micron filtration. Several process parameters within each step, such as pH, temperature, concentration, and time were controlled to serotype-specific values in the sections below.

Polysaccharide Size Reduction and Activation

Purified pneumococcal capsular Ps powder was dissolved in water, and all serotypes, except serotype 19A, were 0.45-micron filtered. All serotypes, except serotypes 18C and 19A, were homogenized to reduce the molecular mass of the Ps. Homogenization pressure and number of passes through the homogenizer were controlled to serotype-specific targets (150-1000 bar; 4-7 passes). Serotype 18C was size-reduced by acid hydrolysis at ≥90° C. Serotype 19A was not size-reduced.

Size-reduced polysaccharide was 0.2-micron filtered and then concentrated and diafiltered against water using a 10 kDa NMWCO tangential flow ultrafiltration membrane. A 5 kDa NMWCO membrane was used for serotype 18C.

The polysaccharide solution was then adjusted to a serotype-specific temperature (4-22° C.) and pH (4-5) with a sodium acetate buffer. Polysaccharide activation was performed via periodate oxidation. Ps activation was initiated with the addition of a sodium metaperiodate solution. The amount of sodium metaperiodate added was serotype-specific, ranging from approximately 0.1 to 0.5 moles of sodium metaperiodate per mole of polysaccharide repeating unit.

For all serotypes, the activated product was diafiltered against 10 mM potassium phosphate, pH 6.4, and water using a 10 kDa NMWCO tangential flow ultrafiltration membrane. A 5 kDa NMWCO membrane was used for serotype 18C. Ultrafiltration for all serotypes was conducted at 2-8° C.

Polysaccharide Conjugation to $CRM_{197}$

Purified $CRM_{197}$, obtained through expression in Pseudomonas fluorescens as previously described (WO 2012/173876 A1), was diafiltered against 2 mM phosphate, pH 7.0 buffer using a 5 kDa NMWCO tangential flow ultrafiltration membrane and 0.2-micron filtered.

The oxidized polysaccharide solution was formulated with water and sucrose in preparation for lyophilization. The protein solution was formulated with water, phosphate buffer, and sucrose in preparation for lyophilization. Sucrose concentrations ranged from 1 to 5% to achieve optimal redissolution in DMSO following lyophilization.

Formulated Ps and $CRM_{197}$ solutions were individually lyophilized. Lyophilized Ps and $CRM_{197}$ materials were redissolved in DMSO and combined using a tee mixer. Sodium cyanoborohydride (1 moles per mole of polysaccharide repeating unit) was added, and conjugation proceeded for a serotype-specific duration (1 to 48 hours) to achieve a targeted conjugate size.

Reduction with Sodium Borohydride

Sodium borohydride (2 mole per mole of polysaccharide repeating unit) was added following the conjugation reaction. The batch was diluted into 150 mM sodium chloride at approximately 4° C. Potassium phosphate buffer was then added to neutralize the pH. The batch was concentrated and diafiltered at approximately 4° C. against 150 mM sodium chloride using a 30 kDa NMWCO tangential flow ultrafiltration membrane.

Final Filtration and Product Storage

Each batch was then concentrated and diafiltered against 10 mM histidine in 150 mM sodium chloride, pH 7.0 at 4° C. using a 300 kDa NMWCO tangential flow ultrafiltration membrane. The retentate batch was 0.2-micron filtered.

Serotype 19F was incubated for approximately 5 days at 22° C., diafiltered against 10 mM histidine in 150 mM sodium chloride, pH 7.0 at approximately 4° C. using a 300 kDa NMWCO tangential flow ultrafiltration membrane, and 0.2-micron filtered.

The batch was diluted with additional 10 mM histidine in 150 mM sodium chloride, pH 7.0 and dispensed into aliquots and frozen at ≤−60° C.

Example 4: In-Process Incubation of Serotype 19F-$CRM_{197}$ Conjugate for Improved Conjugate Stability During routine process development, drug product (DP) stability studies at 4° C. using a serotype 19F-$CRM_{197}$ conjugate prepared as described in Example 3 without incubation (after the 300 kDa ultrafiltration, at final filtration and product storage) showed an initial rapid decline in serotype 19F potency with time (Table 1, conjugate lot A). The relative potency decrease of approximately 20% from initial levels in approximately 3 months revealed that the serotype 19F conjugate was unstable. Note that no such trend was observed for other serotypes. Correspondingly, drug substance (DS) stability studies using the same serotype 19F-$CRM_{197}$ conjugate showed an initial rapid increase in free polysaccharide (Ps) content (FIGS. 1-2, conjugate lot A) and decrease in conjugate size (Tables 2-3, conjugate lot A), indicative of conjugated Ps loss. The initial rapid increase in free Ps was followed by a leveling off in free Ps content, suggests that there is a population of labile sites within the serotype 19F conjugate. These labile sites degrade quickly under typical storage conditions liberating free Ps, reducing conjugate size, and resulting in potency loss. Eventually, when labile sites have degraded, the free Ps and potency changes with time are significantly reduced.

mately 5 days at 22° C. in 150 mM sodium chloride with 10 mM histidine (lot B) or 25 mM potassium phosphate (lot C). A comparison of the stability results for lots A to lots B or C shows that the in-process incubation significantly improved the stability of serotype 19F conjugate.

Figure 3:
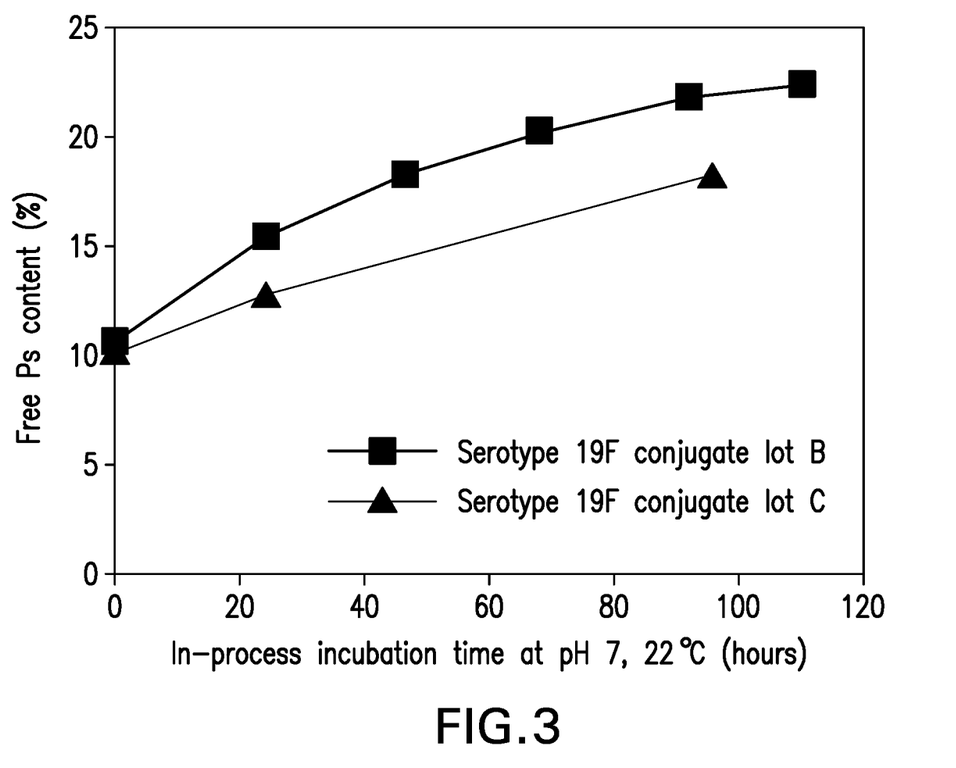
FIG. 3: Free Ps content in two serotype 19F conjugate lots B and C (described in Table 1 and FIG. 2) as a function of time during the in-process incubation step to improve drug substance (DS) and drug product (DP) stability. Free Ps generated during incubation is cleared in subsequent wide-pore ultrafiltration step.

Actual free Ps profile during the in-process incubation of conjugate lots B and C is shown FIG. 3. Results show that free Ps content immediately started to increase during the incubation and later plateaued at roughly 5 days.

TABLE 1

Relative potency, based on total polysaccharide ELISA results, for serotype 19F conjugate lots in DP formulations at 4° C. Serotype 19F conjugate lot B was incubated at 22° C. for approximately 5 days in 10 mM histidine, 150 mM sodium chloride, pH 7.0 prior to wide-pore ultrafiltration purification and DP formulation. Serotype 19F conjugate lot A was not incubated during its production prior to DP formulation.

| Time at 2-8° C. (months) | Relative potency of serotype 19F in DP formulated using non-incubated serotype 19F conjugate lot A | Relative potency of serotype 19F in DP formulated using incubated serotype 19F conjugate lot B |
|---|---|---|
| 0 | 1.0 | 1.1 |
| 3 | 0.8 | 1.1 |

TABLE 2

Serotype 19F conjugate stability as measured by conjugate size change at 4° C. Conjugate size change for serotype 19F-CRM$_{197}$ conjugate lots A and B as a function of time at pH 7.0 and 4° C. Serotype 19F conjugate lots A and B are described Table 1. Conjugate size (Mw) was measured by high performance size exclusion chromatography with UV absorbance, multi-angle light scattering, and refractive index detection (HPSEC UV-MALS-RI).

| Time at 2-8° C. (months) | Conjugate size change, non-incubated serotype 19F conjugate lot A | Conjugate size change, incubated serotype 19F conjugate lot B |
|---|---|---|
| 6 | −44% | −2% |

TABLE 3

Serotype 19F conjugate stability as measured by conjugate size change at 25° C. Conjugate size change for three serotype 19F-CRM$_{197}$ conjugate lots as a function of time at pH 5.8 and 25° C. Serotype 19F conjugate lots A and B are described Table 1; serotype 19F conjugate lot C is described in FIG. 2. Conjugate size (Mw) was measured by HPSEC UV-MALS-RI.

| Time at 25° C. (weeks) | Conjugate size change, non-incubated serotype 19F conjugate lot A | Conjugate size change, incubated serotype 19F conjugate lot B | Conjugate size change, incubated serotype 19F conjugate lot C |
|---|---|---|---|
| 4 | −29% | +4% | +2 |

Figure 1:
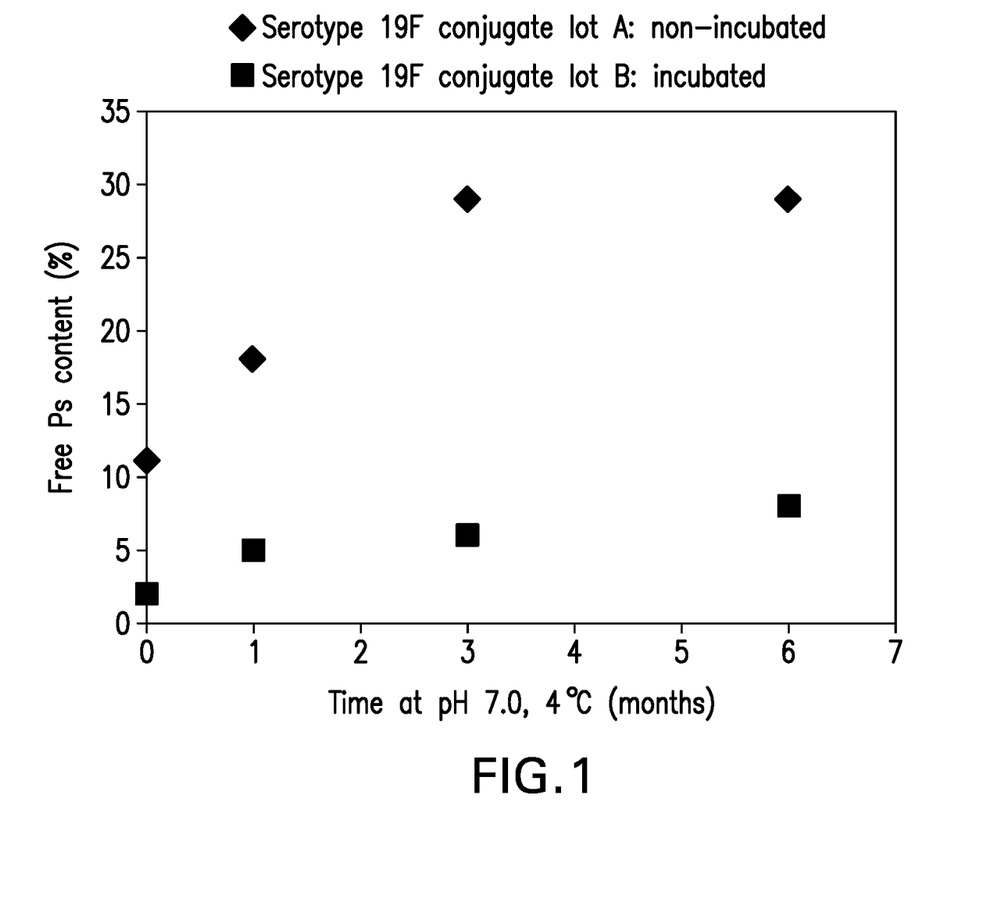
FIG. 1: Serotype 19F conjugate stability as measured by free polysaccharide (Ps) change at 4° C. Free Ps content for two serotype 19F-$CRM_{197}$ conjugate lots as a function of time at pH 7.0 and 4° C. Serotype 19F conjugate lot A was not incubated, lot B was incubated at 22° C. for approximately 5 days prior to wide-pore ultrafiltration purification. See Table 1.
Figure 2:
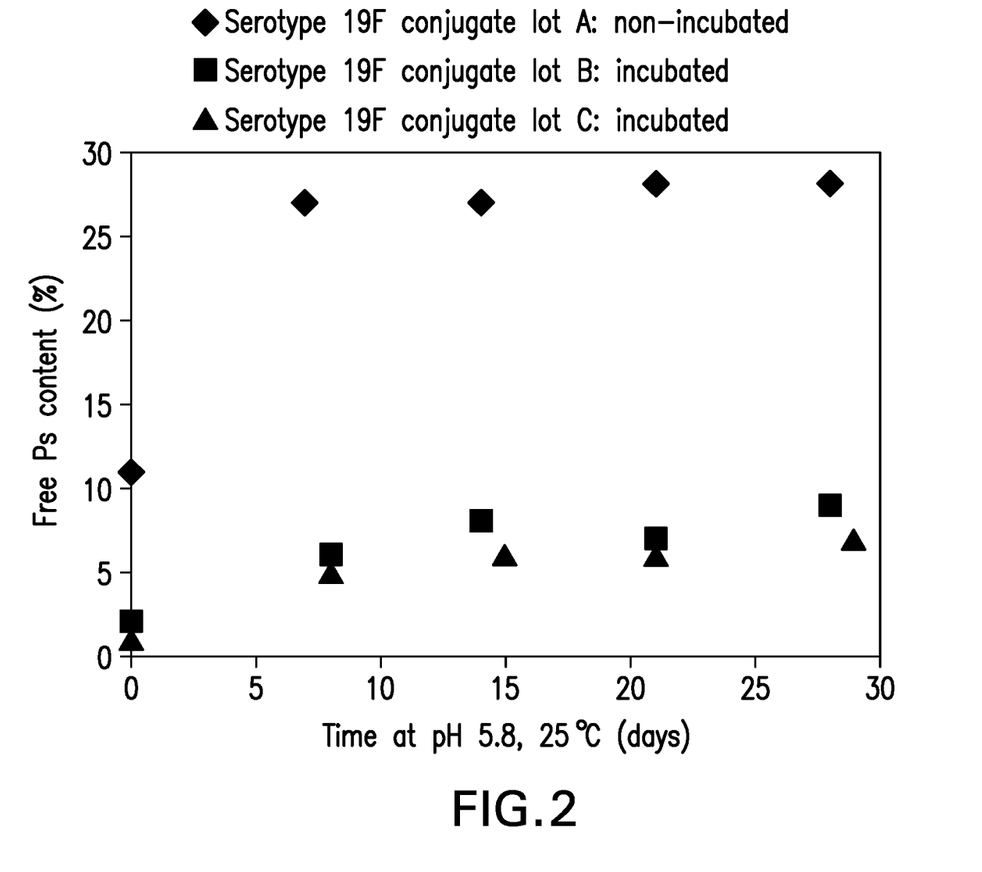
FIG. 2: Serotype 19F conjugate accelerated stability as measured by free Ps change at 25° C. Free Ps content for three serotype 19F-$CRM_{197}$ conjugate lots as a function of time at pH 5.8 and 25° C. Serotype 19F conjugate lot A was not incubated, lot B was incubated at 22° C. for approximately 5 days in 10 mM histidine, 150 mM sodium chloride, pH 7.0 prior to wide-pore ultrafiltration purification. See Table 1. Serotype 19F lot C was incubated at 22° C. for approximately 5 days at pH 7.0 in 25 mM potassium phosphate, 150 sodium chloride prior to wide-pore ultrafiltration purification.

Based on the results for serotype 19F lot A shown in FIGS. 1-2 and Tables 1-2, an in-process incubation step was developed and incorporated in the manufacturing DS process to improve the stability of serotype 19F conjugate. Following the in-process incubation step, conjugates were purified using a wide-pore ultrafiltration step to remove free Ps and low molecular weight conjugates resulting from incubation. The in-process incubation step was conducted after reduction with sodium borohydride and allows liberation and removal of free Ps that would otherwise evolve over time in DS or DP. As described above, serotype 19F conjugate lots B in and C in FIGS. 1-2 and Tables 1-2 had been incubated during their manufacture at pH 7.0 for approxi- In the absence of an incubation step, free Ps would be expected to be generated at a similar rate in the drug substance and/or in the drug product leading to increased levels of free Ps in the vaccine.

A multivalent pneumococcal conjugate vaccine comprising serotype 19F prepared according to the methods of the invention was found to be immunogenic in mice, rabbits, non-human primates and in humans (data not shown).

What is claimed is:

1. A method for the production of a stable *Streptococcus pneumoniae* serotype 19F polysaccharide-CRM197 carrier protein conjugate, wherein the *Streptococcus pneumoniae* serotype 19F polysaccharide-CRM197 carrier protein conjugate comprises *Streptococcus pneumoniae* serotype 19F capsular polysaccharide covalently linked to a CRM197 carrier protein, the method comprising the steps of:
    a) performing a conjugation reaction wherein *Streptococcus pneumoniae* serotype 19F polysaccharide is covalently linked to a CRM197 carrier protein, wherein the conjugation reaction generates a reaction mixture comprising *Streptococcus pneumoniae* serotype 19F polysaccharide-CRM197 carrier protein conjugates and free *Streptococcus pneumoniae* serotype 19F polysaccharides;
    b) incubating said reaction mixture for 5-7 days at a temperature of 20-25° C. in a buffer at a pH of 6.5-7.5; and c) performing size separation under conditions that allow removal of the free *Streptococcus pneumoniae* serotype 19F polysaccharides.

2. The method of claim 1, wherein said size separation uses a nominal molecular weight cut off membrane of from 100 to 500 kDa whereby the *Streptococcus pneumoniae* serotype 19F polysaccharide-CRM197 carrier protein conjugate is retained.

3. The method of claim 1, further comprising d) collecting the *Streptococcus pneumoniae* serotype 19F polysaccharide-CRM197 carrier protein conjugate.

4. The method of claim 2, wherein the retained *Streptococcus pneumoniae* serotype 19F polysaccharide-CRM197 carrier protein conjugate has an average molecular weight of 600 kDa or more.

5. The method of claim 4 wherein the *Streptococcus pneumoniae* serotype 19F polysaccharide-CRM197 carrier protein conjugate has an average molecular weight of 1000 kDa or more.

6. The method of claim 1, wherein said buffer is selected from a phosphate buffer, histidine, and TRIS.

7. The method of claim 1, wherein said size separation is by size-exclusion chromatography, bind/elute chromatography, or wide-pore ultrafiltration.

8. The method of claim 7, wherein said size separation is by wide-pore ultrafiltration with a membrane having a MWCO of 100 kDa to 300 kDa.

\* \* \* \* \*

UNITED STATES PATENT AND TRADEMARK OFFICE
CERTIFICATE OF CORRECTION

| | | |
|---|---|---|
| PATENT NO. | : 11,883,502 B2 | Page 1 of 1 |
| APPLICATION NO. | : 17/544239 | |
| DATED | : January 30, 2024 | |
| INVENTOR(S) | : Michael Albert Winters and John E. MacNair | |

It is certified that error appears in the above-identified patent and that said Letters Patent is hereby corrected as shown below:

On the Title Page

Column 1, Please delete the following:
"Related U.S. Application Data
(63) Continuation of application No. 16/482,337, filed as application no. PCT/US2018/015905 on Jan. 30, 2018, now abandoned"

And replace with:
--Related U.S. Application Data
(63) Continuation of application No. 16/482,337, filed July 31, 2019, which is a 371 National Stage application of International Application No. PCT/US2018/015905, filed January 30, 2018, which claims the benefit of U.S. provisional application no. 62/452,521, filed January 31, 2017.--

Signed and Sealed this
Twelfth Day of March, 2024

Katherine Kelly Vidal
*Director of the United States Patent and Trademark Office*